(12) United States Patent
Bhimavarapu et al.

(10) Patent No.: US 10,235,845 B2
(45) Date of Patent: Mar. 19, 2019

(54) PATIENT SUPPORT APPARATUSES WITH RECONFIGURABLE COMMUNICATION

(71) Applicant: Stryker Corporation, Kalamazoo, MI (US)

(72) Inventors: Krishna Sandeep Bhimavarapu, Kalamazoo, MI (US); Jerald A. Trepanier, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/945,437

(22) Filed: Apr. 4, 2018

(65) Prior Publication Data

US 2018/0293849 A1    Oct. 11, 2018

Related U.S. Application Data

(60) Provisional application No. 62/481,949, filed on Apr. 5, 2017.

(51) Int. Cl.
| | |
|---|---|
| *G08B 5/22* | (2006.01) |
| *A61B 5/00* | (2006.01) |
| *A61G 7/05* | (2006.01) |
| *G16H 40/63* | (2018.01) |

(52) U.S. Cl.
CPC .......... *G08B 5/228* (2013.01); *A61B 5/7465* (2013.01); *A61B 5/7475* (2013.01); *A61G 7/0524* (2016.11); *G16H 40/63* (2018.01)

(58) Field of Classification Search
CPC .............................. A61G 7/012; A61G 2205/60
USPC ..................................................... 340/573.1
See application file for complete search history.

(56) References Cited

U.S. PATENT DOCUMENTS

| | | |
|---|---|---|
| 6,411,742 B1 | 8/2002 | Lovely |
| 7,237,287 B2 | 7/2007 | Weismiller |
| 7,292,135 B2 | 11/2007 | Bixler et al. |
| 8,046,625 B2 | 10/2011 | Ferguson et al. |
| 8,120,470 B2 | 2/2012 | Collins, Jr. et al. |
| 8,120,471 B2 | 2/2012 | Collins, Jr. |
| 8,437,876 B2 | 5/2013 | Receveur et al. |
| 8,536,990 B2 | 9/2013 | Collins, Jr. et al. |
| 8,618,918 B2 | 12/2013 | Tallent et al. |
| 9,253,259 B2 | 2/2016 | Tallent et al. |
| 9,289,336 B2 | 3/2016 | Lambarth et al. |

(Continued)

FOREIGN PATENT DOCUMENTS

| | | |
|---|---|---|
| WO | 9427544 | 12/1994 |

*Primary Examiner* — Fabricio R Murillo Garcia
(74) *Attorney, Agent, or Firm* — Warner Norcross + Judd LLP

(57) ABSTRACT

A patient support apparatus includes a frame, support surface, cable interface, switches, a location detector, and a controller. The switches are electrically coupled to the interface and the controller selects a configuration for the plurality of switches based on a current location of the patient support apparatus within a healthcare facility. Alternatively or additionally, a user interface may display a plurality of identifiers that each identifies a predefined configuration for the switches wherein the controller configures the switches according to an identifier selected by the user. A transceiver on board the patient support apparatus may communicate with different fixed transmitters and the controller may implement different switch configurations based on messages from the different fixed transmitters.

21 Claims, 10 Drawing Sheets

(56) References Cited

U.S. PATENT DOCUMENTS

| | | | |
|---|---|---|---|
| 9,320,662 B2 | 4/2016 | Hayes et al. | |
| 9,513,899 B2 | 12/2016 | Collins, Jr. et al. | |
| 9,572,737 B2 | 2/2017 | McNeely et al. | |
| 2013/0219622 A1* | 8/2013 | Hornbach | A61G 7/012 5/611 |
| 2013/0318716 A1* | 12/2013 | Vanderpohl, III | A61G 7/012 5/600 |
| 2015/0082542 A1* | 3/2015 | Hayes | A61G 7/018 5/600 |
| 2015/0186611 A1 | 7/2015 | George et al. | |
| 2016/0038361 A1 | 2/2016 | Bhimavarapu | |
| 2016/0296143 A1 | 10/2016 | Hayes et al. | |
| 2017/0099198 A1 | 4/2017 | Bhimavarapu | |

* cited by examiner

Pin 1 Bed Monitoring Status On
Pin 2 Read Light
Pin 3 Room Light
Pin 4 Speaker High
Pin 5 Potentiometer Wiper
Pin 6 Bed Exit Status On
Pin 7 Nurse Call Interlock
Pin 8 Audio Transfer -
Pin 9 Audio Transfer +
Pin 10 Interlock +
Pin 11 Interlock -
Pin 12 Bed Monitoring Fowler 30 deg. Alert
Pin 13 No Connect
Pin 14 Potentiometer Low Common
Pin 15 Potentiometer High Common (Std.) / Audio (STV)
Pin 16 Nurse Answer Light +
Pin 17 Bed Monitor Alert
Pin 18 Bed Monitoring Siderail Alert
Pin 19 Nurse Call Light +
Pin 20 No Connect
Pin 21 No Connect
Pin 22 No Connect
Pin 23 Brake Status On
Pin 24 No Connect
Pin 25 Nurse Call +
Pin 26 Nurse Call NO/NC
Pin 27 Room/Read Light Common
Pin 28 Nurse Call Light -
Pin 29 Nurse Answer Light -
Pin 30 Priority NO/NC
Pin 31 Priority Common
Pin 32 Bed Monitoring Low Height Alert
Pin 33 TV - (Std.) / Data (STV)
Pin 34 TV + (Std.) / Common (STV)
Pin 35 Speaker Low Common
Pin 36 Audio Shield
Pin 37 Bed Monitoring Common FIG. 14
(Prior Art)

PATIENT SUPPORT APPARATUSES WITH RECONFIGURABLE COMMUNICATION

CROSS-REFERENCE TO RELATED APPLICATIONS

This application claims priority to U.S. provisional patent application Ser. No. 62/481,949 filed Apr. 5, 2017, by inventors Krishna Bhimavarapu et al. and entitled PATIENT SUPPORT APPARATUSES WITH RECONFIGURABLE COMMUNICATION, the complete disclosure of which is incorporated herein by reference.

BACKGROUND

The present disclosure relates to patient support apparatuses, such as beds, cots, stretchers, operating tables, recliners, wheelchairs, or the like. More specifically, the present disclosure relates to patient support apparatuses that are adapted to communicate with an existing nurse call system and/or one or more room controls.

Existing hospital beds often include an exit detection system that detects when the patient leaves the bed and notifies a nurse call system that the patient has left the bed. Existing hospital beds also often include a nurse call button and speaker that allow the patient to communicate with a remote nurse using the nurse call system. Still other features and/or information regarding the bed may also be communicated to and/or through the nurse call system, or to a room control system that controls various aspects of the room in which the patient support apparatus is positioned (e.g. volume, channel, and power of a television, room temperature, room lights, etc.)

In order for the bed to communicate this information to the nurse call system or the room controls, the bed must be configured in a manner that corresponds to the particular nurse call system and room controls that have been installed in a particular healthcare facility, or a particular room of a healthcare facility. This is because different manufacturers of nurse call systems and room control systems handle communications in different manners. Further, communication between the bed and these systems typically is carried out via a cable running from the bed to a port in a headwall, and the configuration of the headwall port may vary from room to room and/or from healthcare facility to healthcare facility.

SUMMARY

According to various embodiments, the present disclosure provides one or more improved features for expediting and/or reducing the labor associated with configuring a patient support apparatus to enable it to communicate with a particular nurse call system, headwall, and/or room control system. In some aspects, the present disclosure includes a patient support apparatus that is automatically configured according to a predefined configuration setting based on the location of the patient support apparatus. In other aspects, the patient support apparatus may communicate with an off-board device in order to determine its proper configuration. In still other aspects, a user interface may be provided that enables a user to quickly and easily configure the patient support apparatus to communicate with a desired nurse call system and/or headwall.

According to a first embodiment of the present disclosure, a patient support apparatus is provided that includes a frame, a support surface for supporting a patient thereon, an interface, a plurality of switches, a location detector, and a controller. The interface is adapted to couple to a cable having a plurality of electrical conductors. The plurality of switches are electrically coupled to the interface. The controller selects a configuration for the plurality of switches based on a current location of the patient support apparatus within a healthcare facility.

According to other aspects, the location detector includes a wireless transceiver adapted to communicate with a short-range beacon positioned within the healthcare facility at a fixed location off-board the patient support apparatus.

In some embodiments, the patient support apparatus also includes an exit detection system adapted to detect when a patient exits from the support surface. In such embodiments, the controller changes a state of at least one of the switches in response to detecting a patient exiting from the support surface.

A nurse call control is included in some embodiments. The nurse call control is adapted to be activated by the patient and to prompt communication with a remotely positioned nurse when so activated. The controller changes a state of at least one of the switches in response to the nurse call control being activated.

According to other aspects, the patient support apparatus includes a memory having a plurality of configuration settings stored therein; a plurality of location identifiers stored therein; and an index indicating which configuration settings correspond to which location identifiers. A transceiver may also be included that communicates with an off-board device. The controller may be adapted to perform one or more of the following: (1) receive additional location identifiers from the off-board device via the transceiver and to update the index indicating which of the configuration settings correspond to the additional location identifiers; (2) receive additional configuration settings from the off-board device via the transceiver and update the index indicating which of the location identifiers correspond to the additional configuration settings; and/or (3) receive an updated index indicating which of the configuration settings correspond to which of the location identifiers.

In some embodiments, the patient support apparatus further comprises a memory having a plurality of predefined configuration settings stored therein wherein each predefined configuration setting corresponds to a particular commercially available headwall interface.

The interface is adapted to receive a multi-pin connector in some embodiments. The multi-pin connector electrically communicates with the plurality of switches such that a nurse call system off-board the patient support apparatus is able to determine a status of at least some of the switches via signals sent through the multi-pin connector.

According to another embodiment of the present disclosure, a patient support apparatus is provided that includes a frame, a support surface for supporting a patient, an interface adapted to couple to a cable having a multiple electrical conductors, a plurality of switches, a user interface with a display, and a controller. The switches are electrically coupled to the interface. The controller is adapted to display on the display a plurality of identifiers. Each identifier identifies a predefined configuration setting for the plurality of switches. The controller allows a user to select one of the identifiers and to configure the plurality of switches according to the selected one of the identifiers.

In some embodiments, each of the identifiers corresponds to a particular location within a healthcare facility. The identifiers may indicate a name of a particular location within the healthcare facility.

According to other aspects, a transceiver is included that communicates with an off-board device. The controller is adapted to receive additional identifiers via the transceiver. The additional identifiers correspond to additional predefined configuration settings for the plurality of switches. The controller displays on the display the additional identifiers and allows a user to select one of the additional identifiers. The transceiver is a wireless transceiver in some embodiments. The transceiver may also or additionally communicate with a server on a healthcare facility local area network. The server may, in turn, be in communication with a geographically remote server and be adapted to receive from the geographically remote server the additional identifiers and additional predefined configuration settings.

In some embodiments, one or more of the identifiers correspond to a particular commercially available nurse call system.

The user interface may be adapted to allow a user to modify one or more individual switch settings of the predefined configuration settings.

According to another embodiment of the present disclosure, a patient support apparatus is provided that includes a frame, a support surface for a patient, a plurality of switches, an interface, a transceiver, and a controller. The interface is adapted to receive a multi-pin connector that electrically communicates with the plurality of switches such that a nurse call system off-board the patient support apparatus is able to determine a status of at least some of the switches via signals sent through the multi-pin connector. The transceiver is adapted to communicate with a plurality of fixed transmitters. The controller configures the plurality of switches according to a first setting when the transceiver receives a first message from a first one of the fixed transmitters and configures the plurality of switches according to a second setting when the transceiver receives a second message from a second one of the fixed transmitters. The first and second settings are different.

According to other aspects, the patient support apparatus further comprises an exit detection system adapted to detect when a patient exits from the support surface. The controller opens a first one of the switches when configured according to the first setting in response to detecting the patient exiting from the support surface, and the controller closes the first one of the switches when configured according to the second setting in response to detecting the patient exiting from the support surface.

The first message may identify a first location and the second message may identify a second location. The second location is different from the first location.

In some embodiments, the first fixed transmitter includes a unique patient support apparatus identifier in the first message that corresponds to the patient support apparatus and the second fixed transmitter also includes the unique patient support apparatus identifier in the second message.

In any of the embodiments disclosed herein, the patient support apparatus may be one of a bed, a stretcher, a chair, a recliner, a wheelchair, an operating table, or a cot.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 14 is a chart of a prior art example of the functions of the pins of a 37-pin cable often used in existing healthcare facilities.

DETAILED DESCRIPTION OF THE EMBODIMENTS

Figure 1:
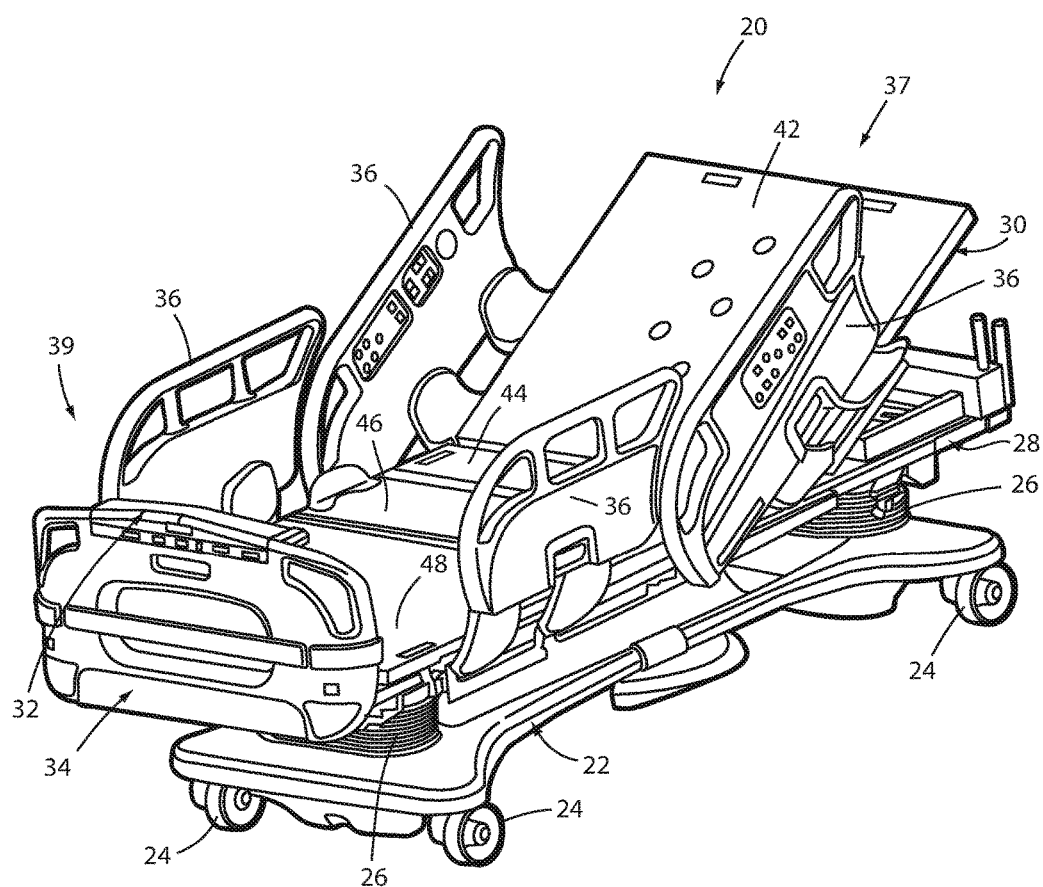
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, an operating table, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 37 and a foot end 39, each of whose height can be independently adjusted by the nearest lift 26. Patient support apparatus 20 is designed so that when an occupant lies thereon, his or her head will be positioned adjacent head end 37 and his or her feet will be positioned adjacent foot end 39.

Litter frame 28 provides a structure for supporting support deck 30, footboard 34, and siderails 36. Support deck 30 provides a support surface for a mattress (not shown in FIG. 1), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Patient support apparatus 20 further includes a user interface 32 that enables a user of patient support apparatus 20, such as a caregiver associated with the patient who occupies patient support apparatus 20, to control one or more aspects of patient support apparatus 20. Such aspects include, but are not limited to, changing a height of support deck 30, raising or lowering head section 42, activating and deactivating a brake for wheels 24, arming and disarming an exit detection system 56 (FIG. 5) and, as will be explained in greater detail below, configuring patient support apparatus 20 to properly communicate with the particular IT infrastructure installed in the healthcare facility in which patient support apparatus 20 is positioned.

User interface 32 is implemented in the embodiment shown in FIG. 1 as a control panel having a lid (flipped down in FIG. 1) underneath which is positioned a plurality of controls. The controls may be implemented as buttons, dials, switches, or other devices. User interface 32 may also include a display 38 (FIG. 5) for displaying information regarding patient support apparatus 20. The display is a touchscreen in some embodiments. Although FIG. 1 illustrates user interface 32 mounted to footboard 34, it will be understood that user interface 32 can be positioned elsewhere.

Figure 2:
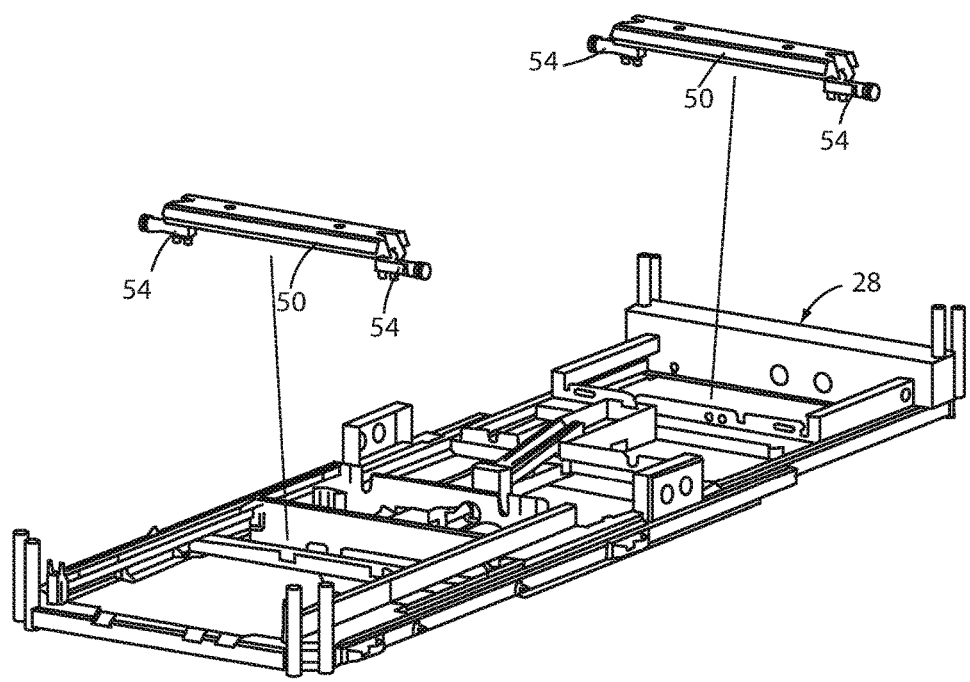
FIG. 2 is a perspective view of a litter and a pair of lift header assemblies with force sensors of the patient support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of force sensors 54, which will be described herein as being load cells, but it will be understood that force sensors 54 may be other types of force sensors besides load cells. The illustrated embodiment of patient support apparatus 20 includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 34, siderails 36, etc.). Because of this construction, load cells 54 are adapted to detect the weight of not only those components of patient support apparatus 20 that are supported by litter frame 28 (including litter frame 28 itself), but also any objects or persons who are wholly or partially being supported by support deck 30.

Figure 3:
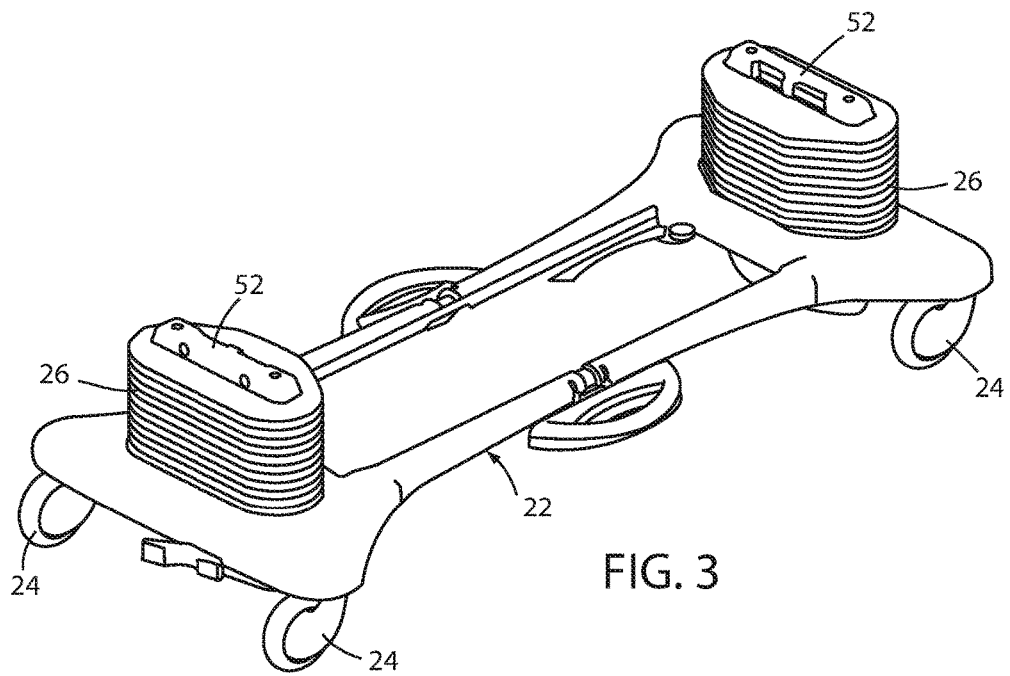
FIG. 3 is a perspective view of a base of the patient support apparatus of FIG. 1.

The mechanical construction of patient support apparatus 20, as shown in FIGS. 1-3, is the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Load cells 54 are part of an exit detection system 56 (FIG. 5) that will be discussed in greater detail below. In general, exit detection system 56, when armed via user interface 32, determines when an occupant of patient support apparatus 20 has left, or is likely to leave, patient support apparatus 20, and issues an alert and/or notification to appropriate personnel so that proper steps can be taken in response to the occupant's departure (or imminent departure) in a timely fashion. In at least one embodiment, exit detection system 56 monitors the center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, exit detection system 56 determines if the occupant is about to exit, or already has exited, from patient support apparatus 20 by determining a distribution of the weights detected by each load cell 54 and comparing the detected weight distribution to one or more thresholds. In such embodiments, the center of gravity may or may not be explicitly calculated.

Other manners for functioning as an exit detection system are also possible. These include, but are not limited to, any of the manners disclosed in the following commonly assigned patent applications: U.S. patent application Ser. No. 14/873,734 filed Oct. 2, 2015, by inventors Marko Kostic et al. and entitled PERSON SUPPORT APPARATUS WITH MOTION MONITORING; U.S. patent publication 2016/0022218 filed Mar. 13, 2014, by inventors Michael Hayes et al. and entitled PATIENT SUPPORT APPARATUS WITH PATIENT INFORMATION SENSORS; and U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosures of all of which are incorporated herein by reference. Further, in some embodiments, load cells 54 may be part of both exit detection system 56 and a scale system that measures the weight of a patient supported on support deck 30. The outputs from the load cells 54 are processed, in some embodiments, in any of the manners disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

Figure 4:
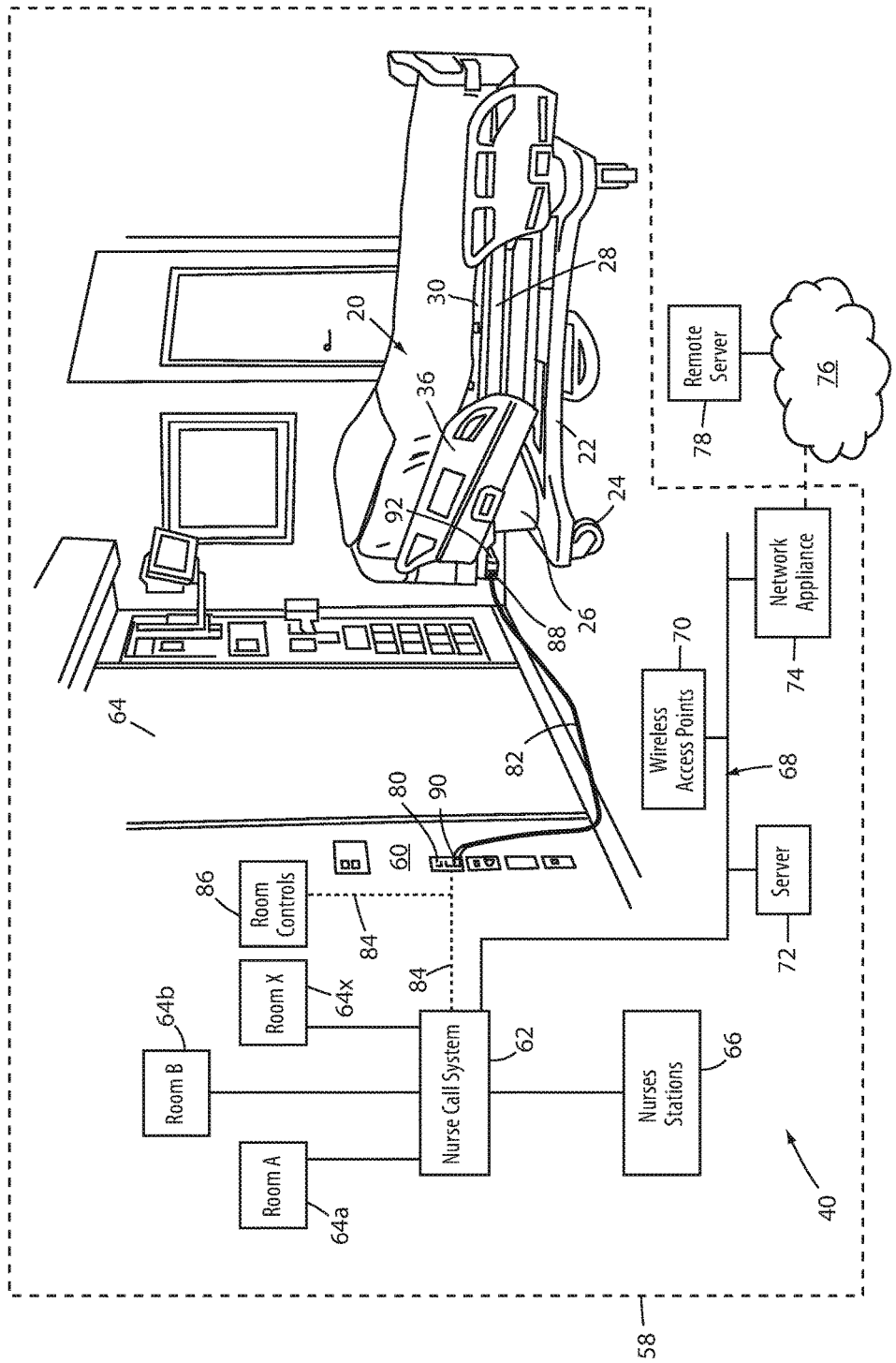
FIG. 4 is a diagram of the patient support apparatus of FIG. 1 shown communicatively coupled to the IT infrastructure of a healthcare facility in a first manner.

FIG. 4 illustrates patient support apparatus 20 coupled to the IT infrastructure 40 of a healthcare facility 58 according to one common configuration. As shown therein, healthcare facility 58 includes a headwall 60, a nurse call system 62, a plurality of rooms 64 (64a, 64b ... 64x), one or more nurses' stations 66, a local area network 68, one or more wireless access points 70, a bed server 72, and one or more network appliances 74 that couple LAN 68 to the internet 76, thereby enabling servers and other applications on LAN 68 to communicate with computers outside of healthcare facility 58, such as, but not limited to, a geographically remote server 78. IT infrastructure 40 also includes one or more room controls 86. It will be understood by those skilled in the art that the particular components of the IT infrastructure 40 of healthcare facility 58 shown in FIG. 4 may vary widely. For example, patient support apparatus 20 may be used in healthcare facilities having no wireless access points 70, no connection to the internet 76 (e.g. no network appliances 74), and/or no bed server 72. Still further, local area network 68 may include other and/or additional servers installed thereon, and nurse call system 62, in some healthcare facilities 58, may not be coupled to the local area network 68. Patient support apparatus 20 is capable of being installed in healthcare facilities 58 having still other variations of the IT infrastructure 40 illustrated in FIG. 4. It will therefore be understood that the particular IT infrastructure 40 shown in FIG. 4 is merely illustrative, and that patient support apparatus 20 is constructed to be communicatively coupled to IT infrastructures arranged differently from that of FIG. 4, some of which are discussed in greater detail below.

Patient support apparatus 20 is coupled to a data port 80 on headwall 60 by way of a cable 82. Data port 80, in turn, is coupled to one or more cables or other conductors 84 that electrically couple the data port 80 to nurse call system 62 and to one or more room controls 86. Conductors 84 are typically located behind headwall 60 and not visible. In some healthcare facilities, conductors 84 may first couple to a room interface board that includes one or more conductors 84 for electrically coupling the room interface board to room controls 86 and/or nurse call system 62. Still other communicative arrangements for coupling data port 80 to nurse call system 62 and/or one or more room controls 86 are possible.

Room controls 86 are conventional room controls that control one or more aspects of the particular room 64 in which the corresponding data port 80 is located. The particular aspects controlled by room controls 86 may vary from healthcare facility to healthcare facility depending upon the particular manufacturer of the room controls 86 and/or the manner in which the room controls have been installed, but generally include such items as controls for an in-room television (e.g. volume, channel, and power), controls for heating or air conditioning, controls for one or more room lights, and/or controls for opening and closing window coverings. Still other room controls may be included. Further, in some embodiments, patient support apparatus 20 may be communicatively coupled to IT infrastructure that includes no room controls 86, and/or that includes room controls 86 in only some rooms, and/or that includes different types of room controls 86 in different rooms.

Cable 82 enables patient support apparatus 20 to communicate with nurse call system 62 and/or room controls 86. A patient supported on patient support apparatus 20 who activates a nurse call control on patient support apparatus 20 causes a signal to be conveyed via cable 82 to the nurse call system 62, which forwards the signal to a one or more remotely located nurses (e.g. nurses at one of the nurses' stations 66). If the patient activates one or more room controls, a signal is conveyed via cable 82 to the room controls 86 that changes one or more aspects of the room in which he or she is located (e.g. change the volume of a television). In order for patient support apparatus 20 to properly communicate with room controls 86 and nurse call system 62, patient support apparatus 20 needs to be configured in a manner that matches the particular room controls 86 and nurse call system 62 that are installed in the particular healthcare facility 58 in which patient support apparatus 20 is located. In other words, different healthcare facilities 58 may utilize different brands and/or models of nurse call systems 62, as well as different brands and/or models of room control equipment. Still further, different healthcare facilities may utilize different types of data ports 80 for communicating with nurse call system 62 and room controls 86. In addition, in some healthcare facilities, different rooms of the healthcare facility may have different types of data ports 80, different room controls 86, and/or be connected to different types of nurse call systems 62.

Patient support apparatus 20 is designed to be more easily configured such that it can communicate with the different data ports 80, room controls 86, and/or nurse call systems 62 that are present in different healthcare facilities and/or in different locations of a particular healthcare facility. In the past, hospital beds and other patient support apparatuses are typically configured for communication with a particular hospital's IT infrastructure at the factory where the beds are made. The configuration often involves choosing the right states for each one of a set of dipswitches that are integrated into the bed. The dipswitches are often not placed at an easily accessible location, are not easily changed if they are inadvertently configured incorrectly, and are not intuitive to set. As will be explained in greater detail below, patient support apparatus 20 is designed to overcome these and/or other disadvantages associated with the configuration of prior art patient support apparatuses.

Figure 12:
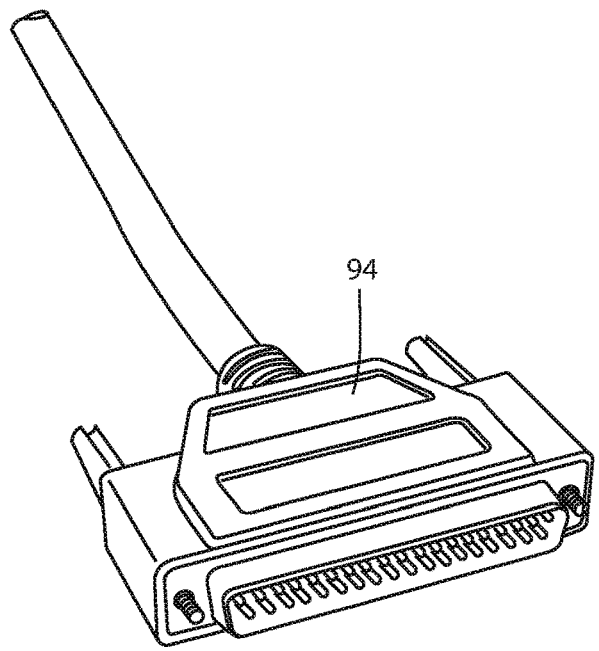
FIG. 12 is a perspective view of a prior art 37-pin male cable connector.
Figure 13:
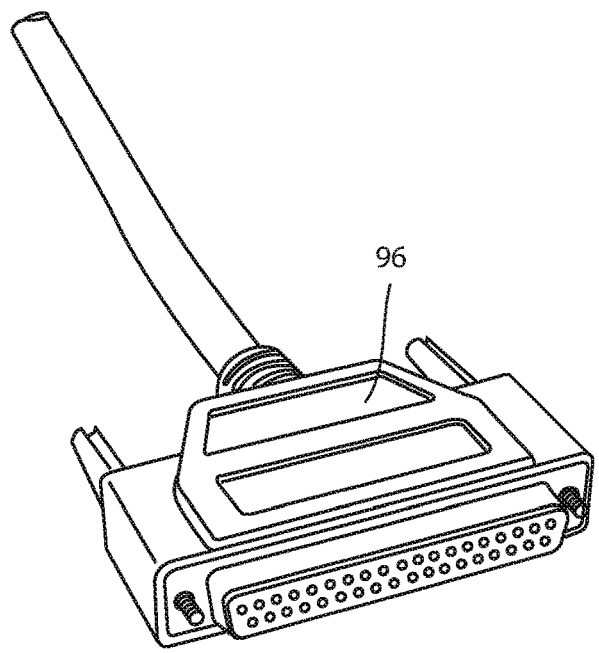
FIG. 13 is a perspective view of a prior art 37-pin female cable connector.

Cable 82 includes a first end having a first connector 88 and a second end having a second connector 90 (FIG. 4). First connector 88 is adapted to be plugged into a cable interface 92 positioned on patient support apparatus 20. Second connector 90 is adapted to be plugged into data port 80. In many healthcare facilities 58, data port 80 is configured as a 37-pin receptacle. In such facilities, cable 82 includes first and second connectors 88 and 90 having 37 pins (one of which may be a male connector and the other of which may be a female connector). One example of a male 37-pin connector 94 that may be used as first or second connector 88 or 90 is shown in FIG. 12. One example of a female 37-pin connector 96 that may be used as first or second connector 88 or 90 is shown in FIG. 13. Other types of 37-pin connectors may also be used, depending upon the configuration of data port 80. Still further, in some healthcare environments, data port 80 includes fewer pins and/or has an arrangement of pins that is shaped differently from what is shown in FIGS. 12 and 13. Patient support apparatus 20 is adapted to communicate with all of these different types of data ports 80 via an appropriately selected cable (e.g. one with the proper connectors 88, 90 on its ends). In combination with the proper cable 82, such communication is enabled by configuring patient support apparatus 20 in one or more of the manners described in more detail below.

Configuring patient support apparatus 20 for proper communication with nurse call system 62 and/or room controls 86 involves supplying patient support apparatus 20 with the knowledge of what data is communicated on each of the pins of data port 80 (and interface 92), what electrical state each of the pins is in when data is not being communicated (e.g. normally open or normally closed), and/or what pins, if any, are not electrically coupled together. One or more of these factors may change when patient support apparatus 20 is used with a different nurse call system 62, a different data port 80, and/or a different set of room controls 86.

Patient support apparatus 20 includes a control system 98 (FIG. 5) that is adapted to be easily configured for communication with different nurse call systems 62, room controls 86, and/or data ports 80. It will be understood that some of the components of control system 98 may be varied from what it shown in FIG. 5, and that, in some modified embodiments, one or more of the components may be omitted entirely. Control system 98 includes a controller 100, one or more sensors 102, a transceiver 104 adapted to wirelessly communicate with one or more off-board devices 106, a nurse call control 108, a room control 110, user interface 32, exit detection system 56, a memory 112, and configuration circuitry 114. Configuration circuitry 114 is electrically coupled to cable interface 92 and controls how interface 92 interacts with cable 82 when first connector 88 of cable 82 is coupled to cable interface 92.

Figure 5:
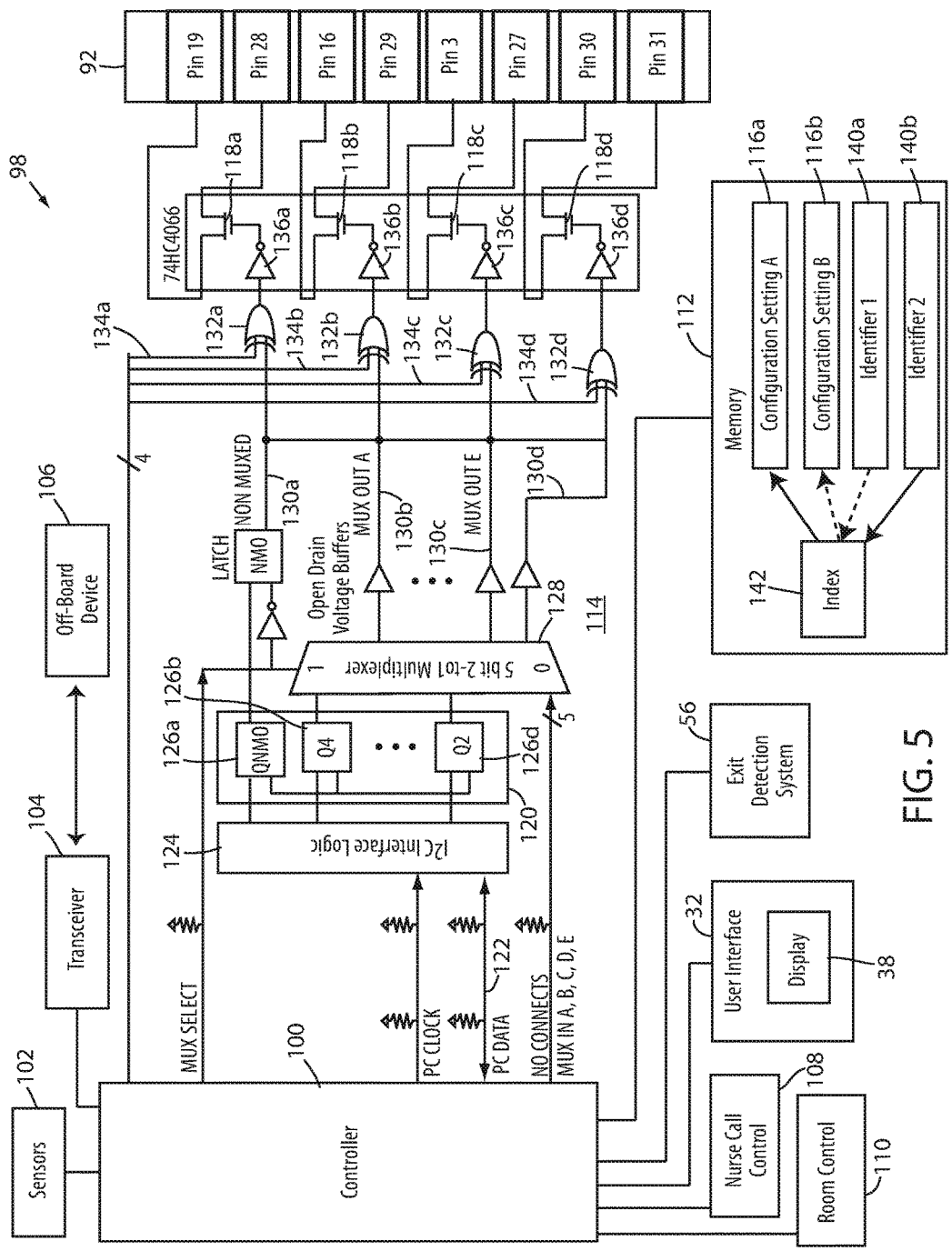
FIG. 5 is a first illustrative embodiment of a control system of the patient support apparatus of FIG. 1.

It will be understood that cable interface 92 is shown in FIG. 5 as having only eight pins. This is done merely for purposes of compact illustration. Cable interface 92 typically includes 37 pins in order to match the number of pins on first connector 88 of cable 82. In such situations, configuration circuitry 114 is expanded from what is shown in FIG. 5 in order to accommodate the additional pins of cable interface 92. This expansion includes a larger memory 120, additional switches 118, and other changes that would be understood by one skilled in the art in light of the following description. In some other embodiments, patient support apparatus 20 may be further modified to include multiple cables interfaces 92 that are adapted to communicate with different style connectors 88. In such embodiments, additional electrical connections are simply added between the configuration circuitry 114 and the additional interfaces.

Each pin of interface 92 is adapted to convey certain information from patient support apparatus 20 to nurse call system 62 and/or room controls 86. FIG. 13 illustrates one illustrative pin assignment for a conventional 37-pin connector. As can be seen in FIG. 13, each pin conveys different information. For example, pin 3 is used to convey information to room controls 86 indicating whether the occupant of patient support apparatus 20 has pressed a control on patient support apparatus 20 to turn on or turn off a light in the particular room in which patient support apparatus 20 is located. In many instances, pin 3 is electrically tied to pin 27 and patient support apparatus 20 commands room controls 86 to turn on or turn off the room light based on whether the connection between pins 3 and 27 is open or closed. For some room controls 86, an open circuit between pins 3 and 27 indicates that the room lights should be turned off and a closed circuit between pins 3 and 27 indicates that the room lights should be turned on. For other room controls, the opposite may be true. That is, for some other room controls 86, an open circuit between pins 3 and 27 indicates the room light should be turned on and a closed circuit between pins 3 and 27 indicates the room lights should be turned off. The different ways in which an open or closed switch or circuit between two or more pins are interpreted by the room controls 86 requires patient support apparatus 20 to be configured to properly communicate with room controls 86 for the particular room patient support apparatus 20 is located in.

In addition to room controls, the various pins of cable interface 92 also communicate information to nurse call system 62. This information is likewise often communicated by opening or closing the electrical connection between two pins. For example, when a patient presses a nurse call control, such as nurse call control 108 (which may be a button, switch, or the like), the electrical connection between pins 19 and 28 is typically changed. These pins indicate to the nurse call system 62 that a nurse call request has been initiated by the occupant of patient support apparatus 20. Depending upon the particular nurse call system 62, it responds by illuminating one or more lights (e.g. a light in the hallway of the healthcare facility and/or a light at one or more of the nurses' stations 66). For some nurse call systems, the connection between pins 19 and 28 should be open when no light is desired and closed when a light is desired, while in other nurse call systems 62 the connection between pins 19 and 28 should be open when a light is desired and closed when no light is desired. Accordingly, patient support apparatus 20 should be configured properly based upon the particular nurse call system 62 with which it is going to communicate.

It will be appreciated that the particular pin numbers illustrated in FIG. 5 are merely an arbitrary selection of pin numbers that have been selected for illustrating the principles of the present disclosure. These selected pin numbers may correspond to the pin numbers illustrated in FIG. 13, or they may correspond to different functions in different embodiments. When implemented to correspond to FIG. 13, switch 118a communicates with pins 19 and 28 to provide information to nurse call system 62 about changing the state of one or more lights associated with a nurse call event. Similarly, when implemented to correspond to FIG. 13, switch 118b communicates with pins 16 and 29 to provide information to nurse call system 62 about when a nurse or other caregiver has answered a nurse call request; switch 118c communicates with pins 3 and 27 to provide information to nurse call system 62 about when a patient has initiated a nurse call; and switch 118d communicates with pins 30 and 31 to provide information to nurse call system 62 about when the patient has exited from patient support apparatus 20. As noted, control system 98 of FIG. 5 may be modified to include additional switches and communication with different pins for conveying different information, as well as altering which pins are coupled to the various switches 118.

In order to configure the normally open or normally closed state of the switches 118 coupled to the pins of cable interface 92, control system 98 utilizes one or more configuration settings 116 stored in memory 112 (FIG. 5). When patient support apparatus 20 first configures cable interface 92, or when changes to the current configuration of cable interface 92 are desired, controller 100 reads one of the configuration settings 116 stored in memory 112. These settings instruct controller 100 how to configure the plurality of switches 118 that are in electrical communication with cable interface 92. Controller 100 configures switches 118 by storing the particular configuration setting read from memory 112 in a non-volatile memory (NVM) 120, which may be an EEPROM (Electrically Erasable Programmable Read-Only Memory) or other type of non-volatile memory. Controller 100 stores the desired configuration setting in NVM 120 by communicating the setting information to NVM 120 using an I-squared-C data bus 122. Data bus 122 communicates with I-squared-C interface logic 124 which is adapted to set the memory elements 126 of NVM 120 in the manners indicating in the configuration setting 116 read from memory 112. Memory elements 126, in turn, are in communication with switches 118 by way of a multiplexor 128. Controller 100 uses the multiplexor 128 to set the neutral state of each of the switches 118. In some embodiments, each memory element 126 identifies the neutral state of a corresponding switch 118. For example, in the embodiment of control system 98 shown in FIG. 5, memory element 126*a* stores the desired neutral state of switch 118*a*, memory element 126*b* stores the desired neutral state of switch 118*b*, and memory element 126*d* stores the desired neutral state of switch 118*d*.

The term "neutral state" used herein refers to the state of a switch 118 when no condition has been detected, or no desired action has been requested by the patient, caregiver, or patient support apparatus 20 itself. Thus, for example, for those pins that communicate an exit detection alert (as detected by exit detection system 56), the neutral state of the corresponding switch 118 is the state of the switch (open or closed) when no patient exit from patient support apparatus 20 has been detected. As another example, for those pins that communicate a change to a room television (channel, volume, power, etc.) or a room light, the neutral state of the corresponding switches 118 refers to the state of those switches 118 when no change is being requested by a user (e.g. the patient has not pressed, or otherwise activated, one of room controls 110).

In the embodiment illustrated in FIG. 5, each switch 118 has been implemented as a MOSFET (Metal Oxide Semiconductor Field Effect Transistor) with its source coupled to one of the pins of cable interface 92 and its drain connected to another of the pins of cable interface 92. Its gate is electrically connected to multiplexor 128 and is either held at a low voltage or a high voltage, depending upon the configuration stored in the corresponding memory element 126 of NVM 120. In other words, the configuration information loaded into NVM 120 by controller 100 dictates whether a high voltage or a low voltage is output on configuration lines 130 of multiplexor 128. Configuration lines 130 each feed into an exclusive OR (XOR) gate 132. The output from each XOR gate 132 is fed to the gate of each switch 118 (after passing through an inverter).

Each XOR gate 132 also has an input connected to a control line 134 whose voltage is determined by controller 100. The voltage on each of control lines 134 is changed by controller 100 in response to a condition that has changed (e.g. a patient exit is detected) or a request being activated (e.g. a nurse call button being pressed). In the absence of any change or request, controller 100 sets control lines 134 to a low voltage. In such a state, the output from each XOR gate 132 is determined by the input that is fed into the XOR gate from configuration lines 130. Configuration lines 130 thus determine the neutral state of the corresponding switch 118. More precisely, configuration lines 130 determine the inverse of the neutral state of the corresponding switch 118 due to the presence of inverters 136.

For example, if line 130*a* is a logic high and control line 134*a* is a logic low, then the output from XOR gate 132*a* will be a logic high and the signal applied to the gate of switch 118*a* will be a logic low (due to inverter 136*a*). On the other hand, if line 130*a* is a logic low and control line 134*a* is a logic low, then the output from XOR gate 132 will be a logic low and the signal applied to the gate of switch 118*a* will be a logic high due to inverter 136*a*. Still further, regardless of whether line 130*a* is high or low, the output from XOR gate 132 will change whenever the state of control line 134*a* changes. That is, if configuration line 130*a* is high and controller 100 changes control line 134*a*, the output from XOR gate 132 will change, and if the configuration line 130*a* is low and controller 100 changes the control line 134*a*, the output from XOR gate 132 will also change. Controller 100 therefore uses control lines 134 to change the state of a switch 118 in response to a change in a condition being detected or a request being activated by a user of patient support apparatus 20.

Control system 98 allows a user to easily change the configuration of switches 118 so that the connections between pairs of pins in their neutral state matches the neutral interpretation made by nurse call system 62 and/or room control system 86. This is accomplished by changing the contents of NVM 120. Thus, for example, if memory element 126*a* is set to cause an output on configuration line 130 that creates a high impedance between the source and drain of switch 118*a* (an effectively open state) when switch 118*a* indicates a neutral state for the parameter reported via pins 19 and 28, and if it is desired to change this neutral configuration of switch 118*a*, this is accomplished by loading a new configuration setting into NVM that changes memory element 126*a* to its opposite (e.g. from high to low, or low to high). This change to memory element 126*a* causes the signal on configuration line 130 to create a low impedance between the source and drain of switch 118*a* (effectively a closed state) for the neutral state. When a condition is detected, or a request is received, by controller 100 that is to be conveyed to nurse call system 62 or room controls 86 via pins 19 and 28, controller 100 changes the state of control line 134*a*, thereby changing the state of the switch 118*a*. It can therefore be seen that NVM 120 determines the neutral states of all of the switches 118 via the logical state of configuration lines 130 while controller 100 changes those neutral states via control lines 134 to the opposite state whenever a condition is detected, or a request is made, that is to be communicated to a corresponding nurse call system 62 or room control 86.

Controller 100 is further programmed to know which control line 134 corresponds to which switch 118 (and its associated pin) so that controller 100 knows which control line 134 to change whenever a condition is detected or a request is made. Thus, for example, if a patient exits patient support apparatus 20, exit detection system 56 sends an exit detection signal to controller 100. In response controller 100 switches the output on whichever control line 134 is coupled to the switch 118 and pin that indicates when an exit alert has been detected. With reference to FIG. 13, the control line 134 that is changed in this example is the control line 134 that is coupled to the switch 118d that is in communication with pins 30 and 31 (priority NO/NC and priority common). When a nurse call system 62 and/or room control system 86 is used that is configured differently from that illustrated in FIG. 13, a different control line 134 may be used.

As evident from FIG. 5, control system 98 is adapted to store multiple configuration settings 116 in memory 112. Each configuration setting specifies the neutral state of each of the switches 118. Each configuration setting 116 may also include additional information, such as pin assignments (e.g. which pin is controlled by which control line 134 and configured by configuration line 130) and/or whether one or more pins should be electrically coupled together or not. In the case of the latter, control system 98 may be modified to include additional switches in front of switches 118 that selectively couple together different pins. For example, if it were desired to couple pin 3 to pin 31, rather than to pin 27 as shown in FIG. 5, configuration circuitry 114 is modified to include switches between configuration lines 130c and 130d and between control lines 134c and 134d. The added switches are controlled by additional control lines whose signals are dictated by additional memory elements stored in NVM 120.

By storing a configuration setting 116 in NVM 120, it is not necessary for controller 100 to retrieve a configuration setting 116 from memory 112 every time controller 100 is powered or rebooted. This enables the state of patient support apparatus 20 to be properly communicated to cable interface 92 without having to wait for controller 100 to read a configuration setting 116 from memory 112 and install the configuration setting in NVM 120. Further, by storing multiple configuration settings 116 in memory 112, controller 100 is able to easily change the configuration settings of patient support apparatus 20 with minimal effort on the part of a user. This enables patient support apparatus 20 to not only be easily configured for a particular healthcare facility, or a particular location of a particular healthcare facility, but also to have its configurations changed when the patient support apparatus 20 is moved to a different location having a different type of nurse call system 62 and/or different room controls 86.

Figure 6:
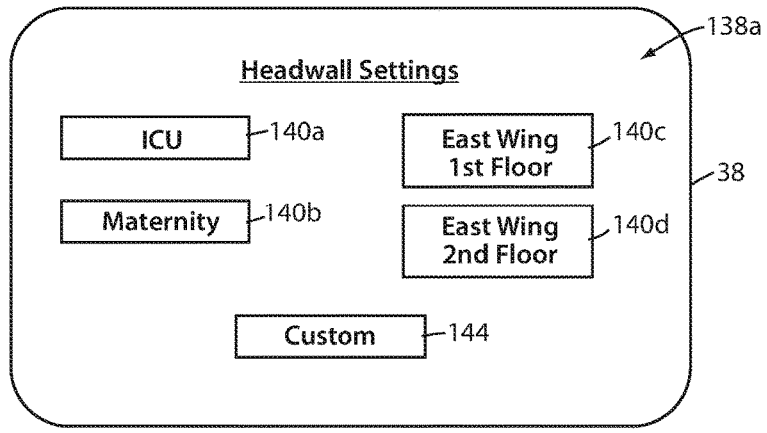
FIG. 6 is a first illustrative screen shot of configuration options displayable on a display of the patient support apparatus.
Figure 7:
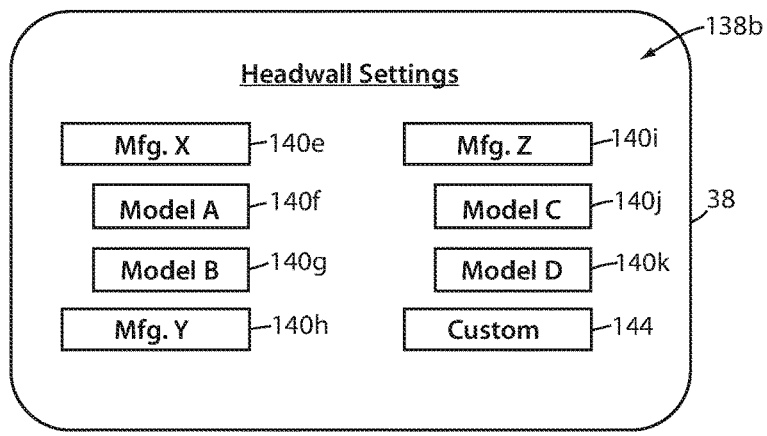
FIG. 7 is a second illustrative screen shot of configuration options displayable on the display of the patient support apparatus.
Figure 8:
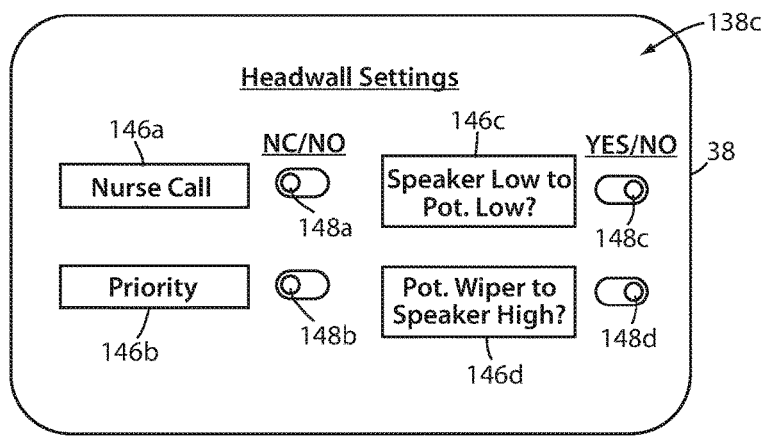
FIG. 8 is a third illustrative screen shot of configuration options displayable on the display of the patient support apparatus.

The different ways in which the configuration of cable interface 92 can be easily changed will now be described in more detail with respect to FIGS. 6-8. FIGS. 6-8 illustrate different representative screen shots 138a-c that are displayable by control system 98 on display 38 of user interface 32. The style, layout, content, and design of these particular screen shots 138a-c may change depending upon the particular embodiment of patient support apparatus 20, the particular healthcare facility in which patient support apparatus 20 is located, and/or the different makes and/or models of nurse call systems 62 and/or room controls 86. It will therefore be understood that screen shots 138a-c are provided merely as illustrative examples for explaining various principles of the present disclosure.

Screen shot 138a of FIG. 6 illustrates a plurality of predefined configuration settings that are each identified by a unique identifier 140. In this particular example, identifiers 140a-d identify different locations within a particular healthcare facility 58. Identifier 140a identifies an intensive care unit; identifier 140b identifies a maternity ward; identifier 140c identifies a particular structural section of the healthcare facility; and identifier 140d identifies a different structural section of healthcare facility 58. It will be understood that the number of location identifiers 140 shown in FIG. 6 may vary, as well as the content of the identifiers. In general, screen shot 138a displays those locations of a healthcare facility 58 where the nurse call system 62 and/or the room controls 86 are configured differently from other sections of the healthcare facility 58. When a patient support apparatus 20 is moved to one of these locations, it is easily configured by having a user select the identifier 140 that corresponds to the particular location of patient support apparatus 20.

For example, if patient support apparatus 20 is moved to the maternity ward of a healthcare facility 58, in order to configure patient support apparatus 20 properly for communicating with the nurse call system 62 and room controls 86 installed in that location of the healthcare facility, a user only needs to select identifier 140b (maternity). In some embodiments, display 38 is a touch screen display and the selection of identifier 140b is accomplished by touching the area of display 38 where identifier 140b is located. In other embodiments display 38 may be implemented differently and a different manner of selecting maternity identifier 140b may be used.

In response to a user selecting a particular identifier 140 from screen shot 138a, user interface 32 sends a signal to controller 100 indicating which identifier 140 was selected by the user. Controller 100 consults an index 142 stored in memory 112 that identifies which identifier 140 corresponds to which configuration setting 116. In some embodiments, such as shown in FIG. 5, memory 112 also stores the various identifiers 140. However, in other embodiments, memory 112 does not store the identifiers 140. In such embodiments, controller 100 uses the identifier received from user interface 32 to identify, via index 142, which configuration setting 116 should be loaded into NVM 120. Controller 100 then loads the corresponding configuration setting 116 into NVM 120.

It will be understood that, although FIG. 5 illustrates only two different configuration settings 116a and 116b, as well as only two different identifiers 140a and 140b, these numbers may vary from embodiment to embodiment and from healthcare facility to healthcare facility. In the example shown in FIG. 6, there would likely be four configuration settings 116a-d, one for each of the identifiers 142a-d. However, this too may vary. For example, if the maternity ward and the first floor of the east wing of the healthcare facility 58 happened to have the same nurse call system 62 and room controls 86, then memory 112 could be modified to only store one configuration setting 116 that corresponded to both locations. In such a situation, controller 100 modifies index 142 such that both identifiers 140b (maternity) and 140c ($1^{st}$ floor, east wing) are linked to the same configuration setting (e.g. 116b). In this particular case, controller 100 might therefore only store three configuration settings. Still other variations are possible.

Control system 98 therefore facilitates the movement of patient support apparatus 20 to different locations within a healthcare facility 58 that communicate with differently configured nurse call systems 62, headwalls 60, and/or room controls 86. This is accomplished by selecting the identifier 140 from screen shot 138 that matches the current location of patient support apparatus 20. Once selected, controller 100 automatically reconfigures patient support apparatus 20 according to the selected location, thereby enabling patient support apparatus 20 to properly communicate with the nurse call system 62, headwall 60, and room controls 86 in that selected location.

Screen shot 138a also includes a custom icon 144. Custom icon 144 is selected by a user whenever the user wishes to change index 142 or one or more of the configuration settings 116 associated with the locations identified by identifiers 140a-d, and/or if the user wishes to add new locations or delete existing locations. For example, if a user with the proper administrative access (control system 98 may be designed so that custom icon 144 is only accessible to certain authorized individuals) wishes to change one or more of the switch 118 settings associated with configuration setting 116a, he may select custom 144 and proceed to a screen shot like that shown in FIG. 8, which enables the user to change individual switch states within a particular configuration setting 116, as will be explained in greater detail below. Selecting custom icon 144 also allows a user to add new identifiers 140 for different locations within healthcare facility 58 and/or to delete one or more of the existing locations 140a-d. Whatever changes are made in response to the user selecting custom icon 144, controller 100 makes corresponding adjustments to index 142 and/or configuration settings 116 in memory 112.

In addition to, or as an alternative to, loading an individual configuration setting 116 using the custom icon 144, patient support apparatus 20 may be adapted to receive configuration settings 116 in different manners. For example, in some embodiments, control system 98 is adapted to receive configuration settings 116, an index 142, and/or identifiers 140 from an off-board device 106 (FIG. 5). In some embodiments, the off-board device 106 corresponds to bed server 72 (FIG. 4), while in other embodiments the off-board device corresponds to a different device. When receiving configuration information (settings 116, index 142, and/or identifiers 140) from bed server 72, controller 100 communicates with bed server 72 via wireless communication with one or more access points 70 of local area network 68. In such situations, transceiver 104 may be a WiFi transceiver, or it may be another type of transceiver adapted to communicate wirelessly with local area network 68 and bed server 72. In still other embodiments, transceiver 104 may be a wired transceiver, such as an Ethernet transceiver, that is adapted to communicate with a wired Ethernet connection to local area network 68. Still other manners of communicating with bed server 72 are possible.

When patient support apparatuses 20 are configured based upon configuration information sent from bed server 72, it may not be necessary to individually configure each patient support apparatus 20. For example, some healthcare facilities 58 include only a single type of nurse call system 62, headwall 60, and room controls 86. In such embodiments, bed server 72 is able to send the corresponding configuration setting 116 to all patient support apparatuses 20 with instructions to implement that particular configuration setting 116. In situations where healthcare facility 58 includes two or more types of nurse call systems 62 (or variations in headwalls 60 or room controls 86), bed server 72 may be configured to send both of the configuration settings 116 that are used in that particular healthcare facility along with an instruction as to which of those multiple configuration settings 116 each particular patient support apparatus 20 is supposed to load into its NVM 120. The instruction of which configuration setting 116 to implement is based upon the current location of each patient support apparatus 20, and this location may be determined in multiple different manners. Examples of some such suitable manners are disclosed in commonly assigned U.S. patent application Ser. No. 14/559,458 filed Dec. 3, 2014, by inventors Michael Hayes et al. and entitled PATIENT SUPPORT APPARATUS COMMUNICATION SYSTEMS, the complete disclosure of which is incorporated herein by reference. Other suitable manners for determining the locations of each patient support apparatus 20 are disclosed in commonly assigned U.S. Pat. No. 8,461,982 issued Jun. 11, 2013, to David Becker et al, the complete disclosure of which is also incorporated herein by reference. Still other manners for determining the location of each patient support apparatus 20 may be used.

Bed server 72 is in communication with one or more user interfaces (e.g. computer terminals, keyboards, displays, etc.) that enable an administrator of the healthcare facility, or an authorized representative, to send the appropriate configuration settings 116 to each of the patient support apparatuses 20. This enables all of the patient support apparatuses 20 to be configured from one central location by inputting information into bed server 72 a single time. This greatly simplifies prior art methods of configuring patient support apparatuses 20 wherein a technician was often required to physically change dipswitch settings on each individual patient support apparatus.

In addition to sending configuration settings 116 to patient support apparatus 20 and an instruction as to which one of the configuration settings 116 to implement, bed server 72 may be further modified to send additional instructions to patient support apparatuses 20 to switch their configuration settings 116, as necessary, as they move throughout the healthcare facility 58. In other words, in some embodiments, bed server 72 is programmed to automatically cause patient support apparatuses 20 to switch from one configuration setting 116 to another configuration setting 116 based upon changes in the location of the patient support apparatus 20. When bed server 72 is programmed in this manner, it is no longer necessary for a user to bring up screen shot 138a on user interface 32 and manually select one of the location identifiers 140a-d when patient support apparatus 20 is moved from one of those locations to another. Instead, the location of the patient support apparatus 20 is repetitively monitored by bed server 72 (using any of the methods mentioned above) and if patient support apparatus 20 moves from a first location to a second location that has a differently configured nurse call system 62, headwall 60, and/or room controls 86, bed server 72 automatically sends a message to that patient support apparatus instructing it to load the configuration settings 116 into NVM 120 that corresponds to the second location. Manual changes of a patient support apparatuses' headwall configuration are therefore automatically made from a centralized location (bed server 72) rather than manually made at each individual patient support apparatus 20 via user interface 32.

Screen shot 138b of FIG. 7 illustrates a plurality of predefined configuration settings that are each identified by a unique identifier 140e-k. In this particular example, identifiers 140e-k identify different manufacturers and models of nurse call systems 62, data ports 80, and/or room controls 86. In order to configure patient support apparatus 20 for proper communication with the nurse call system 62, data port 80, and/or room controls 86 of a particular room, the user manipulates user interface 32 to bring up screen shot 138b and selects therefrom the appropriate manufacturer and/or model of the nurse call system 62, data port 80, and/or room controls 86. It will be understood that the number of manufacturer identifiers 140e-k shown in FIG. 7 may of course vary, as well as the content of the identifiers. In some embodiments, screen shot 138b displays (or provides controls for displaying) all of the known manufacturers of nurse call systems 62, data ports 80, and/or room controls 86 that require different configuration settings for switches 118. A user then selects from this global list the manufacturer and model that matches what is installed in a particular healthcare facility, or a particular location of a healthcare facility. In other embodiments, only a local list of those manufacturers and models that are installed in a particular healthcare facility are displayed on screen shot 138b. In still other embodiments, other sets of manufacturers and models may be displayed.

After a user selects the particular manufacturer and/or model identifier 140e-k (FIG. 7), the user's selection is forwarded to controller 100. Controller 100 then uses an index, such as index 142, to determine which configuration setting 116 corresponds to the particular manufacturer and/or model selected by the user. After selecting the corresponding configuration setting 116, controller 100 reads the configuration setting from memory 112 and loads its corresponding data into non-volatile memory 120. Once loaded therein, configuration circuitry 114 ensures that switches 118 are properly configured in their appropriate neutral states. Thereafter, if controller 100 detects an alert or other event that requires communication via cable interface 92, controller 100 changes the state of the appropriate switch(es) by sending signal(s) along one or more of the corresponding control lines 134.

Control system 98 may include multiple indexes 142. In some embodiments, control system 98 includes a first index 142 that matches together configuration settings 116 with location identifiers 140, and a second index 142 that matches together configuration settings 116 with manufacturer/model identifiers 140. In still other embodiments, index 142 may also or alternatively match locations with manufacturers and models, or vice versa. In such embodiments, controller 100 may first determine (or be told by another device or instructed by a user) the current location of patient support apparatus 20 within healthcare facility 58. Using this location data, controller 100 consults a first index 142 to determine that that particular location has a particular nurse call system 62. After determining the particular nurse call system, controller 100 may then consult a second index that matches that particular nurse call system 62 to a particular configuration setting 116.

As with screen shot 138a, screen shot 138b includes custom icon 144. When selected, custom icon 144 allows a user to manually change any one or more of the predefined configuration settings 116. Such changes include changes to the neutral switch settings of individual switches 118 for one or more configuration settings 116. In addition, custom icon 144 allows a user to create additional configuration settings 166, as well as the identifiers associated with those configuration settings 116. The created identifiers may be manufacturer and model identifiers, or they may be different types of identifiers. Custom icon 144 further allows a user to enter the data that defines any of the predefined configuration settings 116, although such data may more easily be uploaded to control system 98 during manufacture of patient support apparatus 20. Alternatively, or additionally, the configuration settings 116 associated with the manufacturer/model identifiers (e.g. identifiers 140e-k of FIG. 7) may be uploaded to individual patient support apparatuses 20 via communication with bed server 72, and/or with a remote server 78, the latter of which may be controlled by the same entity that manufacturers patient support apparatuses 20. In such situations, configuration settings 116 may be first downloaded from remote server 78 to bed server 72, and from bed server 72 to the individual patient support apparatuses 20 within healthcare facility 58. Other means for loading the configuration settings 116 are also possible.

FIG. 8 illustrates a screen shot 138c that, unlike screen shots 138a and 138b of FIGS. 6 and 7, respectively, does not show a plurality of identifiers 140 corresponding to a plurality of predefined configuration settings 116. Instead, FIG. 8 illustrates a plurality of individual switch identifiers 146a-d. Switch identifiers 146a-d correspond to the state of individual switches 118. Thus, screen shot 138c allows a user to select the states of individual switches 118, rather than a predefined configuration setting 116 that defines the states for the entire set of switches 118. Screen shot 138c is therefore one example of the type of screen shot that may be displayed in response to a user selecting custom icon 144 from screen shots 138a and 138b.

Although screen shot 138c only illustrates four switch identifiers 146a-d, it will be understood that the actual number of switch identifiers 146 displayable on display 38 of user interface 32 will generally be at least as great as the total number of switches 118 that are present on patient support apparatus 20. This allows a user to select the neutral state for each of the switches 118 present on patient support apparatus 20. In the example shown in FIG. 8, the user selects the individual state of a particular switch using a corresponding radio button 148, which is positioned next to the switch identifier 146. For example, if the user wants the nurse call switch 118 to be in a normally open state, the user slides radio button 148a to the right (to the NO state). If the user wants the nurse call switch 118 to be in a normally closed state, the user slides the radio button 148a to the position shown in FIG. 8. Similarly, if the user wants the speaker low pin electrically coupled to the potentiometer low pin, the user slides radio button 148c to the left to the YES position. If this electrical connection is not desired, the user keeps radio button 148c in the NO position, as shown in FIG. 8. Choices for the rest of the switch identifiers 146 are made in a similar way, including additional switch identifiers 146 that are not shown on screen shot 138c.

In addition to the information shown in FIG. 8, controller 100 may also be programmed to display a location identifier 140 and/or a manufacturer/model identifier 140 on screen shot 138c. That is, in some embodiments, controller 100 initially displays all of the switch identifiers 146 with their corresponding radio buttons 148 positioned in whichever state is the normal or default state for a particular location and/or a particular manufacturer/model. Thereafter, a user can change any one or more of those switch settings by sliding the corresponding radio button 148 to a different state. In this manner, screen shot 138c can be used to customize any of the predefined configuration settings 116 discussed above.

The content of screen shot 138c therefore may change, depending upon which particular set of predefined configuration settings 116 a user has selected. For example, if a user selects maternity identifier 140b from screen shot 138a of FIG. 6 and then selects the custom icon 144, controller 100 displays a screen shot 138c that illustrates switch identifiers 146 with their associated radio buttons 148 in the positions used in the maternity ward. The user can then make changes to any of these individual switch settings, if desired. On the other hand, if the user selects east wing, second floor identifier 140d from screen shot 138a, controller 100 displays a screen shot 138c that illustrates switch identifier 146 and their associated radio buttons 148 in the positions used for the second floor of the east wing. The user can then make changes to any of these individual switch settings. Screen shot 138c therefore can be used to display the switch settings currently in use by patient support apparatus 20 and/or the switch settings associated with any of the other identifiers 140 (location and manufacturer/model).

It will be understood by those skilled in the art that control system 98 may be implemented with many different variations, including, but not limited to, one or more of the following. Instead of using MOSFETs for one or more of switches 118, different types of transistors may be used, or relays may be used, or still other types of switches may be used. Instead of communicating configuration information from controller 100 to NVM 120 over an I-Squared-C bus 122, other types of communication busses may be used (e.g. Controller Area Network (CAN) bus, a Local Interconnect Network (LIN) bus, Firewire, RS-232, RS-485, a Universal Serial Bus (USB), Ethernet, and/or a Serial Peripheral Interface (SPI) bus), as well as non-bus communication. NVM 120 may also be implemented in other manners besides EEPROM. Still other variations are possible.

Controller 100 may take on a variety of different forms. In the illustrated embodiment, controller 100 is implemented as one or more conventional microcontrollers. However, controller 100 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by 100 when carrying out the functions described herein, as well as the data necessary for carrying out these functions, are stored in memory 112 and/or another memory accessible to controller 100.

It will also be understood that the data communicated from patient support apparatus 20 to nurse call system 62 and/or room controls 86 via cable interface 92 may include data beyond what has been explicitly discussed so far. Such data includes all of the data displayed in FIG. 13, as well any additional data that is desirably communicated via cable interface 92. Some examples of additional data that may be communicated via switches 118 and cable interface 92 include: whether one or more siderails 36 are in a down position (or an up position); whether the position of any of the siderails 36 changes from an initial state; whether a brake on patient support apparatus 20 is set; whether exit detection system 56 is armed; whether support deck 30 is at its lowest height; whether head section 42 has pivoted to less than a threshold angle (e.g. 30 degrees); and whether patient support apparatus 20 has been set or not to monitor a particular set of conditions. These various items of data are detected by one or more corresponding sensors 102 that communicate with controller 100 (FIG. 5).

Figure 9:
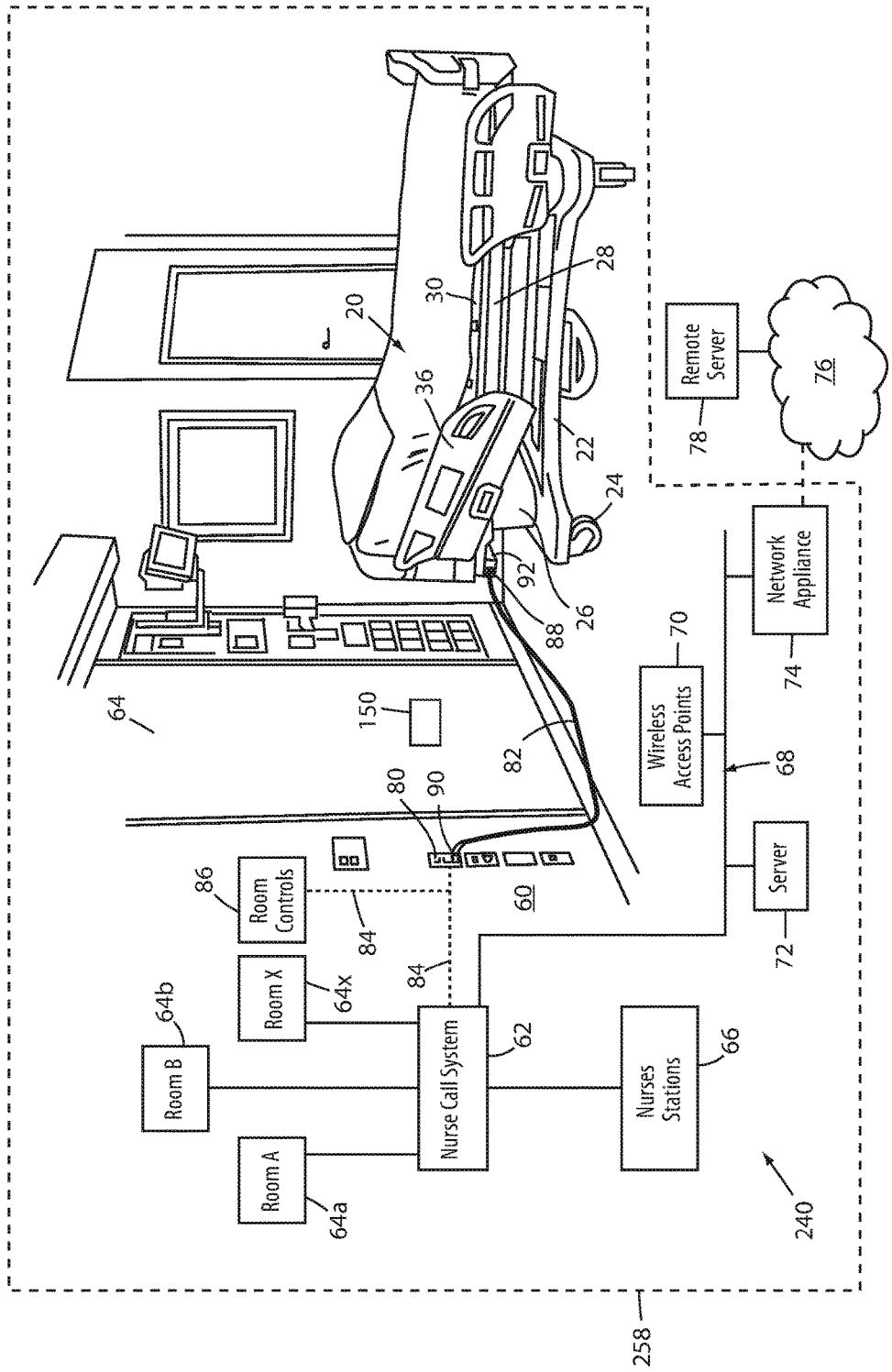
FIG. 9 is a diagram of the patient support apparatus of FIG. 1 shown communicatively coupled to the IT infrastructure of a healthcare facility in a second manner.

FIG. 9 illustrates patient support apparatus 20 coupled to an alternative set of IT infrastructure 240 of a healthcare facility 258 according to another type of configuration. IT infrastructure 240 of FIG. 9 differs from IT infrastructure 40 of FIG. 4 in that IT infrastructure 240 includes one or more location beacons 150 that are mounted at fixed locations within rooms 64, such as, but not limited to, the headwalls 60 of rooms 64. Typically, a beacon 250 is mounted adjacent each data port 80 so that anytime a patient support apparatus 20 is connected by a cable to a data port 80, it is in communication with an adjacent beacon 250.

Beacons 250 are adapted to wirelessly communicate with patient support apparatuses 20 over a relatively short distance, such as approximately 3-10 feet. Using such short range communication (which may involve infrared communication, Bluetooth, Bluetooth LE, near field communication, combinations of these technologies, and/or other types of short range communication), a patient support apparatus 20 is only able to communicate with a nearby beacon 250 when the patient support apparatus 20 is within a short distance of the beacon 250. The ability of a particular patient support apparatus 20 to communicate with a particular beacon 250 therefore provides a proxy indication that that particular patient support apparatus 20 is located adjacent that particular beacon 250. By assigning each beacon 250 a unique identifier and by mapping the location of each beacon 250 within a particular healthcare facility 58, it is possible to determine the location of a particular patient support apparatus 20 based upon its communication with a nearby beacon 250.

Patient support apparatus 20 is configured, in at least one embodiment, to receive a unique identifier from beacon 250 when the patient support apparatus 20 is positioned nearby. This identifier is received, in some embodiments, via transceiver 104. In other embodiments, the control system 98 of patient support apparatus 20 is modified to include a separate transceiver for communicating with beacon 250. Still further, in some embodiments, beacon 250 initially communicates with patient support apparatus 20 using a short range receiver, and thereafter communicates with patient support apparatus 20 using a longer range transceiver. In order to ensure that the long range communications are not misinterpreted by another patient support apparatus 20 within the vicinity, beacon 250 may receive a unique identifier from the patient support apparatus 20 via the short range communications and use the identifier in the long range communications. Any patient support apparatuses 20 that receive the long range messages, but which don't have the same patient support apparatus identifier, ignore those messages. Still other communication protocols may be used.

Regardless of the manner in which patient support apparatus 20 receives the unique identifier from beacon 250, controller 100 uses the unique identifier to select which configuration setting 116 to install into NVM 120. This selection may be carried out in different manners.

In one embodiment, memory 112 includes an index 142 that matches each of the unique beacon identifiers to specific configuration settings 116. In another embodiment, memory 112 includes a first index that matches the beacon identifier to a location identifier, and controller 100 uses a second index 142 to match the location identifier to a specific configuration setting 116. In still another embodiment, controller 100 sends the beacon identifier to bed server 72 and bed server 72 determines the location of the patient support apparatus 20 via a table that maps beacon identifiers to specific locations within healthcare facility 58. Bed server 72 then sends the corresponding location of the beacon 250 back to patient support apparatus 20 and controller 100 uses the location to select a particular configuration setting 116 (based on a location-to-configuration index 142 maintained in memory 112). In still another variation, controller 100 sends the beacon identifier to bed server 72 and bed server 72 responds by sending the appropriate configuration setting 116 back to patient support apparatus 20.

In still another embodiment, beacon 250 transmits directly to patient support apparatus 20 the appropriate configuration setting 116 that is to be used by patient support apparatus 20 for that particular location of healthcare facility 58. In this embodiment, if patient support apparatus 20 is later moved to a different location of healthcare facility 58 that requires different configuration settings for communicating with nurse call system 62, room controls 86, or data port 80, patient support apparatus 20 receives the required configuration settings from the beacon 250 positioned adjacent the particular data port 80 at that different location. In this embodiment, beacons 250 may include their own transceivers (e.g. WiFi) that communicate with one or more wireless access points 70 and receive from bed server 72 the appropriate configuration settings 116 that are to be used at their corresponding locations within healthcare facility 58. Alternatively, beacons 250 may receive their corresponding configuration setting 116 in other manners.

Figure 10:
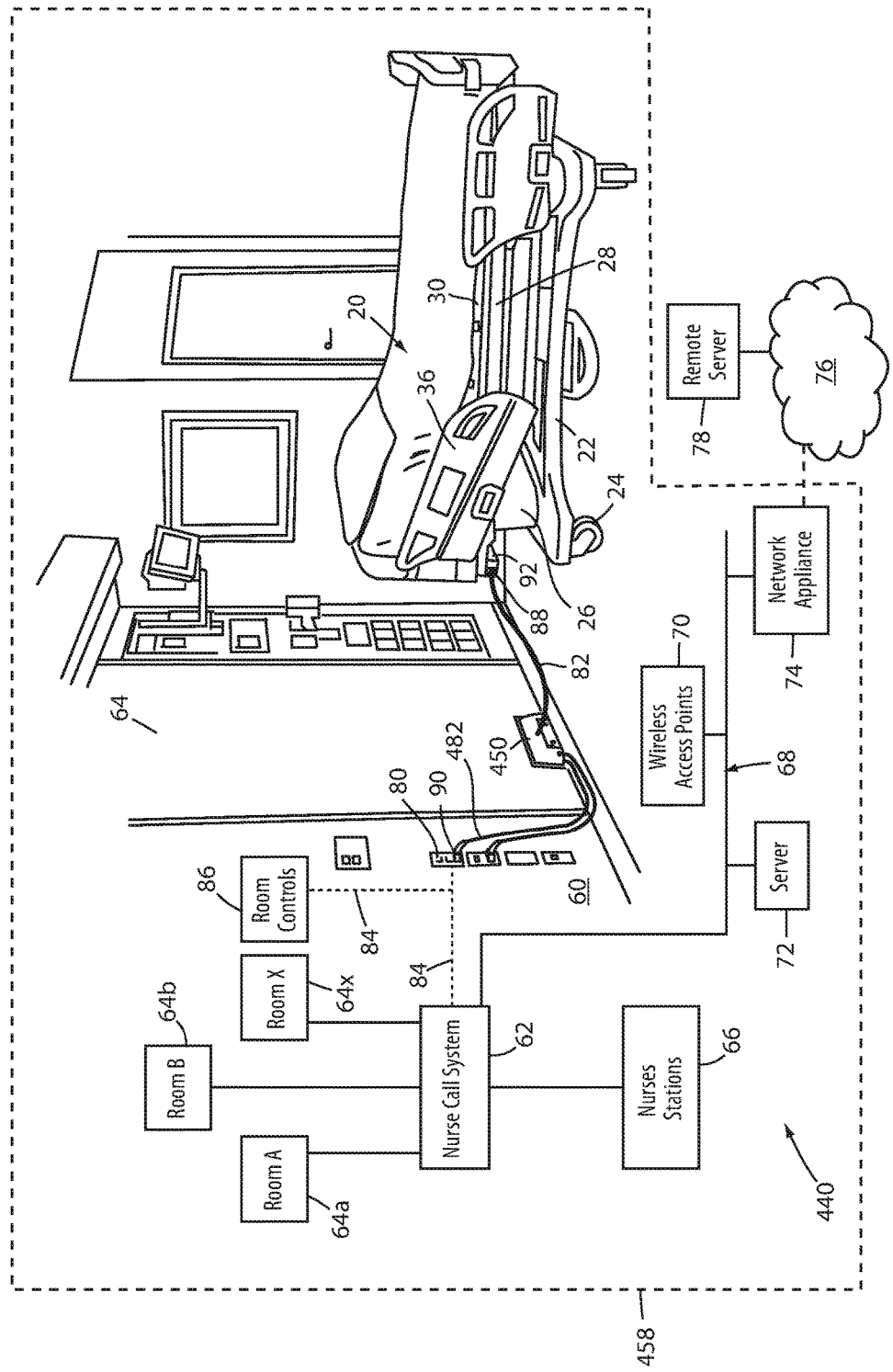
FIG. 10 is a diagram of the patient support apparatus of FIG. 1 shown communicatively coupled to the IT infrastructure of a healthcare facility in a third manner.

FIG. 10 illustrates patient support apparatus 20 coupled to an alternative set of IT infrastructure 440 of a healthcare facility 458 according to another type of configuration. IT infrastructure 440 of FIG. 10 differs from IT infrastructure 240 of FIG. 9 in that IT infrastructure 440 includes one or more adapter beacons 450 that are mounted at fixed locations within rooms 64, such as, but not limited to, the headwalls 60 of rooms 64. As with location beacons 250, adapter beacons 450 are typically mounted adjacent each adjacent each data port 80 so that anytime a patient support apparatus 20 is connected by a cable to a data port 80, it is in communication with an adjacent beacon 450.

Adapter beacons 450 are similar to location beacons 250 in that adapter beacons 450 provide location information to patient support apparatuses 20. This location information may be provided wirelessly, as with beacons 250, or it may be provided via cable 82, which is coupled between patient support apparatus 20 and the associated adapter beacon 450. Also, adapter beacons 450, like location beacons 250, are stationary and remain in fixed locations that are mapped during installation such that the location of each adapter beacon 450 is known.

Adapter beacons 450 differ from location beacons 250 in that adapter beacons 450 receive cables 82 from patient support apparatuses 20 and adjust, if necessary, the manner in which data received from the patient support apparatuses 20 is communicated to data ports 80. In making these adjustments, adapter beacons 450 are adapted to be differently configured so that they are able to communicate with different types of nurse call systems 62, room controls 86 and/or data ports 80. By using adapter beacons 450, it is not necessary for patient support apparatus 20 to be reconfigured when it moves to a different location within healthcare facility 458 that uses a different type of nurse call system 62, room control 86, and/or data port 80. Instead, the adapter beacons 450 are configured in a manner that matches the particular nurse call system 62, room controls 86, and data port 80 installed for the room in which they are located. This ensures proper communication between the patient support apparatus 20 and the IT infrastructure 440 without requiring the patient support apparatuses 20 to be reconfigured when moved to different locations.

In some embodiments, adapter beacons 450 include a memory, configuration circuitry, switches, a controller, and a cable interface similar to the memory 120, configuration circuitry 114, switches 118, controller 100, and cable interface 92 of control system 98 of patient support apparatus 20. In these embodiments, the controller of the beacon 450 installs in the memory 120 the proper switch settings so that controller 100 is able to properly communicate via its cable interface with the nurse call system 62, room controls 86, and data port 80. That is, controller 100 receives data from patient support apparatus 20 via cable 82 and then changes the state of one or more of its own switches based on the data received from patient support apparatus 20. These switches are in electrical communication with a second cable 482 (FIG. 10) that extends between adapter beacons 450 and data port 80. Data port 80 therefore receives data that is properly configured for successful communication with its connected nurse call system 62 and room controls 86.

Adapter beacons 450 therefore offload from patient support apparatuses 20 the necessity of the patient support apparatuses 20 being properly configured for communication with different IT infrastructures. Instead, all of the patient support apparatuses 20 can be commonly configured to communicate with adapter beacons 450. Adapter beacons 450 may then handle any conversion of the data communicated from (or to) patient support apparatus 20 that is necessary for successful communication with the particular nurse call system 62 and room controls 86 installed in a particular room of healthcare facility 58.

Patient support apparatuses 20 that are adapted to communicate with adapter beacons 450 may therefore omit the configuration circuitry 114 shown in FIG. 5, although such circuitry may be included in patient support apparatuses 20 in order for the patient support apparatus 20 to communicate in locations where an adapter beacon 450 may not be present. In some embodiments, the configuration settings of a particular adapter beacon 450 are both displayable and changeable using user interface 32 of patient support apparatus 20. In such embodiments, any or all of the features discussed above with respect to predefined configuration settings 116 and/or changing those configuration settings in conjunction with FIGS. 6-8 may be still present on patient support apparatus 20, but modified so that the displayed and/or changed configuration settings 116 refer to those of adapter beacon 450 instead of patient support apparatus 20 itself. In this manner, patient support apparatus 20 functions as a tool for changing and viewing the configuration settings of adapter beacons 450.

In an alternative embodiment of adapter beacons 450, each adapter beacon 450 is able to communicate individually with one or more servers on local area network 68. In such embodiments, each adapter beacon 450 may include a WiFi transceiver, or other type of transceiver, that is in communication with local area network 68. The configuration settings for a particular adapter beacon are then communicated directly to the adapter beacon 450 via its connection to local area network 68, rather than using a patient support apparatus 20 as an intermediary. The communicated configuration settings for the adapter beacons 450 may come from bed server 72, another server on local area network 68, or from remote server 78.

Figure 11:
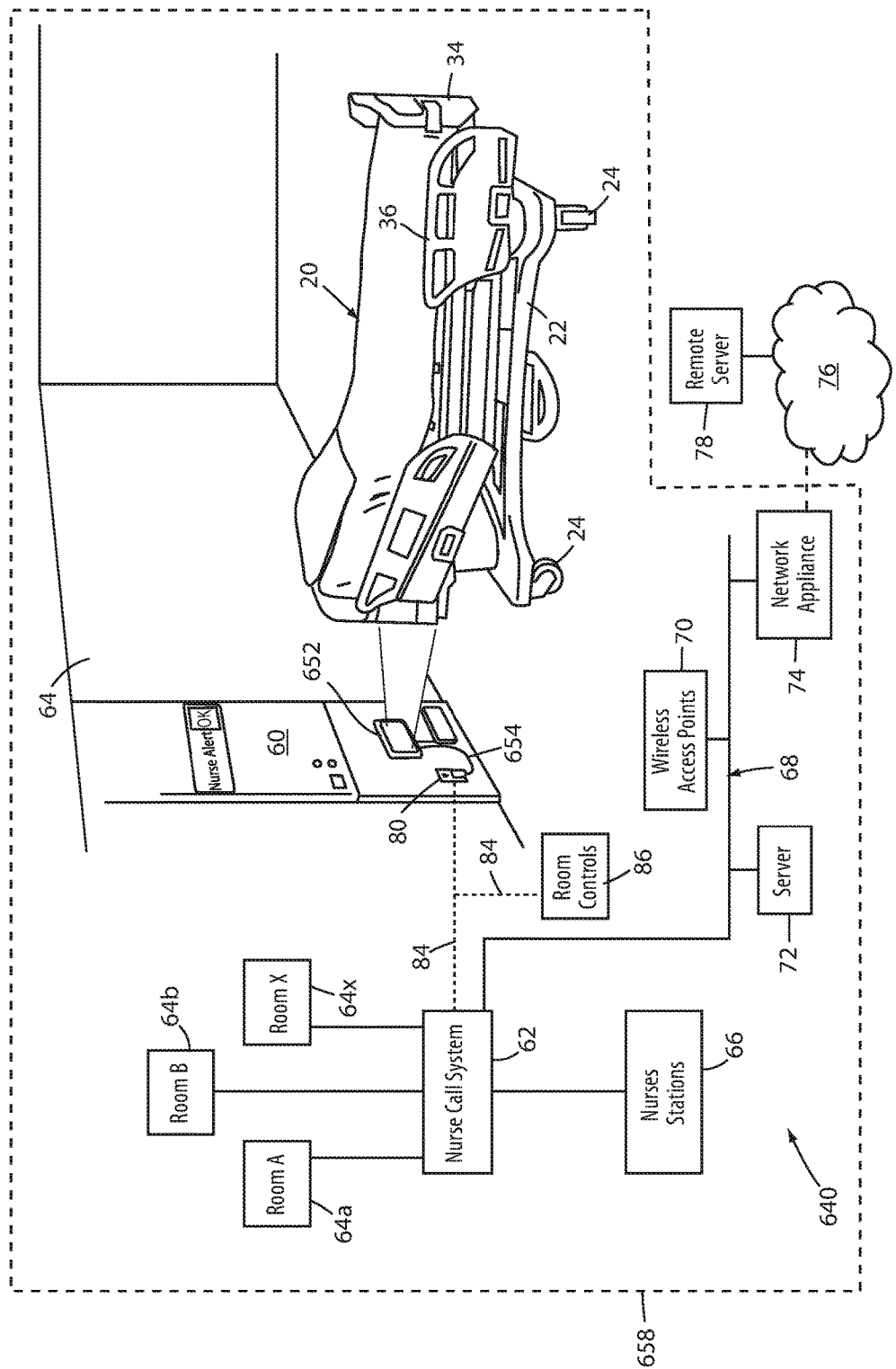
FIG. 11 is a diagram of the patient support apparatus of FIG. 1 shown communicatively coupled to the IT infrastructure of a healthcare facility in a fourth manner.

FIG. 11 illustrates patient support apparatus 20 coupled to yet another alternative set of IT infrastructure 640 of a healthcare facility 658 according to another type of configuration. IT infrastructure 640 of FIG. 11 differs from IT infrastructures 40, 240, and 440 in that IT infrastructure 640 includes one or more wireless headwall units 652 that are mounted at fixed locations within rooms 64, such as, but not limited to, the headwalls 60 of rooms 64. As with location beacons 250 and adapter beacons 450, wireless headwall units 652 are typically mounted adjacent each data port 80 so that anytime data from a patient support apparatus 20 is desirably communicated to a data port, the wireless headwall unit 652 and patient support apparatus 20 are able to communicate.

Wireless headwall unit 652, as its name suggests, enables a patient support apparatus 20 to communicate wirelessly with the data port 80 of the associated headwall. Wireless headwall unit 652 communicates wirelessly with patient support apparatus 20 and communicates via a cable 654 with data port 80. Wireless headwall unit 652, as with adapter beacon 450 and location beacon 250, may be adapted to provide location information to patient support apparatus 20, thereby enabling patient support apparatus 20 to communicate its location to server 72 via a wireless access point 70.

Wireless headwall units 652, like adapter beacons 450, convert the data received wirelessly from patient support apparatus 20, if necessary, into whatever form is necessary for successful communication with the associated nurse call system 62 and/or room controls 86. Similarly, any data that is transmitted from room controls 86 and/or nurse call system 62 to patient support apparatus 20 is first received by wireless headwall unit 652 and, if necessary, converted to a format understandable by patient support apparatus 20. Wireless headwall units 652 perform a similar function to adapter beacons 450 but include the added ability to communicate wirelessly with patient support apparatuses 20. When installed in a healthcare facility that includes wireless headwall units 652, patient support apparatuses 20 may be modified to omit the configuration circuitry 114 of control system 98. Alternatively, patient support apparatuses 20 may retain this circuitry in case a wireless headwall adapter malfunctions or a cable coupled between data port 80 and patient support apparatus 20 otherwise becomes necessary for communication with data port 80.

In some embodiments, wireless headwall units 562 are constructed to include any or all of the functionality of the wireless headwall units disclosed in commonly assigned copending U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. This functionality is in addition to the configuration functionality discussed above that converts data received from patient support apparatus 20 into the proper format for communicating with data port 80.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
   a frame;
   a support surface adapted to support a patient thereon;
   an interface adapted to couple to a multi-pin connector of a nurse call cable, the nurse call cable adapted to couple to a nurse call system;
   a plurality of switches electrically coupled to the interface;
   a memory in which is stored a plurality of predefined configuration settings defining neutral states for the plurality of switches;
   a location detector; and
   a controller adapted to receive location data from the location detector wherein the location data is indicative of a current location of the patient support apparatus in a healthcare facility, to select a predefined configuration setting from amongst the plurality of predefined configuration settings based upon the location data received from the location detector, and to use the selected predefined configuration setting for communicating status data of the patient support apparatus to the nurse call system via the plurality of switches and the interface.

2. The patient support apparatus of claim 1 wherein the location detector includes a wireless transceiver adapted to communicate with a short-range beacon positioned within the healthcare facility at a fixed location off-board the patient support apparatus.

3. The patient support apparatus of claim 1 further comprising an exit detection system adapted to detect when a patient exits from the support surface, wherein the controller changes a state of at least one of the switches in response to detecting a patient exiting from the support surface.

4. The patient support apparatus of claim 1 further comprising a nurse call control adapted to be activated by the patient and to prompt communication with a remotely positioned nurse when activated, wherein the controller changes a state of at least one of the switches in response to the nurse call control being activated.

5. The patient support apparatus of claim 1 further comprising a memory having a plurality of location identifiers stored therein and an index indicating which configuration settings correspond to which location identifiers.

6. The patient support apparatus of claim 5 further comprising a transceiver adapted to communicate with an off-board device, wherein the controller is adapted to receive additional location identifiers from the off-board device and update the index indicating which of the configuration settings correspond to the additional location identifiers.

7. The patient support apparatus of claim 5 further comprising a transceiver adapted to communicate with an off-board device, wherein the controller is adapted to receive additional configuration settings from the off-board device and update the index indicating which of the location identifiers correspond to the additional configuration settings.

8. The patient support apparatus of claim 5 further comprising a transceiver adapted to communicate with an off-board device, wherein the controller is adapted to receive an updated index indicating which of the configuration settings correspond to which of the location identifiers.

9. The patient support apparatus of claim 5 wherein each predefined configuration setting corresponds to a particular commercially available headwall interface.

10. A patient support apparatus comprising:
    a frame;
    a support surface adapted to support a patient thereon;
    an interface adapted to couple to a multi-pin connector of a nurse call cable, the nurse call cable adapted to couple to a nurse call system;
    a plurality of switches electrically coupled to the interface;
    a memory in which is stored a plurality of predefined configuration settings defining neutral states for the plurality of switches;

a user interface having a display; and a controller adapted to display on the display a plurality of identifiers, each identifier identifying a location and corresponding to a particular predefined configuration setting from amongst the plurality of predefined configuration settings, the controller further adapted to allow a user to select one of the identifiers and to configure the plurality of switches according to the particular predefined configuration setting corresponding to the selected one of the identifiers, the controller further being adapted to use the particular predefined configuration setting for communicating status data of the patient support apparatus to the nurse call system via the plurality of switches and the interface.

11. The patient support apparatus of claim 10 wherein each of the identifiers indicates a name of a particular location within a healthcare facility.

12. The patient support apparatus of claim 10 further comprising a transceiver adapted to communicate with an off-board device, wherein the controller is adapted to receive additional identifiers for additional predefined configuration settings for the plurality of switches, to display on the display the additional identifiers, and to allow a user to select one of the additional identifiers.

13. The patient support apparatus of claim 12 wherein the transceiver is a wireless transceiver and the off-board device is a server on a healthcare facility network.

14. The patient support apparatus of claim 13 wherein the server is in communication with a geographically remote server and adapted to receive from the geographically remote server the additional identifiers and additional predefined configuration settings.

15. The patient support apparatus of claim 10 further comprising a transceiver adapted to communicate with an off-board device, wherein the controller is adapted to transmit to the off-board device a patient support apparatus identifier uniquely identifying the patient support apparatus and to receive the predefined configuration settings from the off-board device.

16. The patient support apparatus of claim 10 wherein each of the identifiers corresponds to a particular commercially available nurse call system.

17. The patient support apparatus of claim 16 wherein the user interface is adapted to allow a user to modify one or more individual switch settings of the predefined configuration settings.

18. A patient support apparatus comprising:
a frame;
a support surface adapted to support a patient thereon;
a plurality of switches;
an interface adapted to receive a multi-pin connector that electrically communicates with the plurality of switches such that a nurse call system off-board the patient support apparatus is able to determine a status of at least some of the plurality of switches via signals sent through the multi-pin connector;
a transceiver adapted to communicate with a remote server and receive a first setting or a second setting from the remote server, each of the first and second settings defining neutral states for the plurality of switches;
a memory in which the first or second setting is stored after receipt from the remote server; and
a controller adapted to configure the plurality of switches according to the first setting when the transceiver receives a first message from the remote server and to configure the plurality of switches according to the second setting when the transceiver receives a second message from the remote server, wherein the controller transmits status data of the patient support apparatus to the nurse call system via the plurality of switches and the interface.

19. The patient support apparatus of claim 18 further comprising an exit detection system adapted to detect when a patient exits from the support surface, wherein the controller opens a first one of the switches when configured according to the first setting in response to detecting the patient exiting from the support surface; and wherein the controller closes the first one of the switches when configured according to the second setting in response to detecting the patient exiting from the support surface.

20. The patient support apparatus of claim 18 wherein the first message identifies a first location and the second message identifies a second location.

21. The patient support apparatus of claim 18 wherein the transceiver is a wireless transceiver.

* * * * *